(12) United States Patent
Asakura

(10) Patent No.: US 9,782,113 B2
(45) Date of Patent: Oct. 10, 2017

(54) LANCING DEVICE

(71) Applicant: Sysmex Corporation, Kobe-shi, Hyogo (JP)

(72) Inventor: Yoshihiro Asakura, Kobe (JP)

(73) Assignee: SYSMEX CORPORATION, Kobe-shi, Hyogo (JP)

(*) Notice: Subject to any disclaimer, the term of this patent is extended or adjusted under 35 U.S.C. 154(b) by 303 days.

(21) Appl. No.: 14/192,465

(22) Filed: Feb. 27, 2014

(65) Prior Publication Data

US 2014/0249561 A1    Sep. 4, 2014

(30) Foreign Application Priority Data

Mar. 1, 2013 (JP) .................................. 2013-041223

(51) Int. Cl.
| | |
|---|---|
| *A61B 5/151* | (2006.01) |
| *A61B 5/15* | (2006.01) |
| *A61B 5/145* | (2006.01) |

(52) U.S. Cl.
CPC ........ *A61B 5/15113* (2013.01); *A61B 5/1519* (2013.01); *A61B 5/150022* (2013.01); *A61B 5/15117* (2013.01); *A61B 5/15128* (2013.01); *A61B 5/150412* (2013.01); *A61B 5/150503* (2013.01); *A61B 5/150984* (2013.01); *A61B 5/14532* (2013.01)

(58) Field of Classification Search
CPC .............. A61B 5/15188; A61B 5/1519; A61B 5/15194; A61B 5/15196; A61B 5/15198; A61B 5/15113; A61B 5/1411; A61B 5/1444; A61B 5/14532; A61B 5/157
USPC .................................................. 606/181, 182
See application file for complete search history.

(56) References Cited

U.S. PATENT DOCUMENTS

| | | | |
|---|---|---|---|
| RE32,922 E * | 5/1989 | Levin ................... | A61B 5/1411 606/182 |
| 2001/0027327 A1 | 10/2001 | Schraga | |
| 2003/0018282 A1 | 1/2003 | Effenhauser et al. | |
| 2003/0088261 A1 | 5/2003 | Schraga | |
| 2004/0249405 A1 | 12/2004 | Watanabe et al. | |
| 2004/0249425 A1* | 12/2004 | Roy ....................... | A61N 1/403 607/99 |

(Continued)

FOREIGN PATENT DOCUMENTS

| | | |
|---|---|---|
| CN | 1547452 A | 11/2004 |
| JP | 2009-11704 A | 1/2009 |
| JP | 2011-177523 A | 9/2011 |

*Primary Examiner* — Tuan V Nguyen
(74) *Attorney, Agent, or Firm* — Brinks Gilson & Lione

(57) ABSTRACT

A lancing device includes: a cover section, a part of which is provided with an opening; a main body held on the cover section and configured to be movable in a predetermined direction from the opening relative to the cover section; a lancing unit which is launched in the predetermined direction; and an operating section configured to launch the lancing unit when the operating section is pushed by applying a force in the predetermined direction, wherein the lancing unit is launched when the force is applied to the operating section in the predetermined direction with regulating a movement of the main body in the predetermined direction, and the main body moves, instead of pushing the operating section, by applying the force in the predetermined direction without regulating the movement of the main body in the predetermined direction is disclosed.

17 Claims, 11 Drawing Sheets

(56) References Cited

U.S. PATENT DOCUMENTS

| | | | |
|---|---|---|---|
| 2004/0260326 A1* | 12/2004 | Lipoma | A61B 5/1411 606/182 |
| 2008/0109025 A1* | 5/2008 | Yang | A61B 5/15142 606/182 |
| 2009/0054920 A1 | 2/2009 | Zhong | |

* cited by examiner

LANCING DEVICE

RELATED APPLICATIONS

This application claims priority under 35 U.S.C. §119 to Japanese Patent Application No. 2013-041223 filed on Mar. 1, 2013, the entire content of which is hereby incorporated by reference.

FIELD OF THE INVENTION

The present invention relates to a lancing device for forming pores for body fluid extraction in the body of a subject.

BACKGROUND OF THE INVENTION

There are well known lancing devices for puncturing the body of a subject with needles to form pores in the skin to extract bodily fluids to be used for measuring components such as glucose in the body fluid of the subject (for example, refer to U.S. Patent Application Publication No. 2009/0054920 and Japanese Patent Application Publication No. 2011/177523).

U.S. Patent Application Publication No. 2009/0054920 discloses a lancing device provided with an end cap at one end of a tubular housing, and a lancet opening in the end cap, whereby a needle-like lance can advance and retract through the lancet opening. This lancing device has structural elements which are user accessible on the side surface of the housing, and is configured so that a spring exerts a force on the lance causing the lance to extend from the lancet opening when the user presses the user accessible structural element on the side of the housing.

Japanese Patent Application Publication No. 2011/177523 discloses a lancing device having a cover section at one end of a cylindrical housing and an operating cap at the other end, and further having a through-hole provided in the cover so that a lancet set needle unit can advance and retract from the through-hole. The lancing device has an operating cap which is slidable in the axial direction of the housing, and is configured so that the sporing exerts a force on the lancet set when the operating cap is pushed on the side of the housing causing the needle unit of the lancet set to protrude from the through-hole of the cover section in the lancing direction.

The lancing device disclosed in U.S. Patent Application Publication No. 2009/0054920 has caused concern that the user accessible structural element may inadvertently operate when the user holds the housing because the direction in which the user holds the housing is the same as the direction of operation of the user accessible structural element. The lancing device disclosed in Japanese Patent Application Publication No. 2011/177523 has caused concern that the user may inadvertently expose the sharp lancet set needle unit from the end of the cover section when the user operates the operating cap while the cover section is not abutting the body of the user (subject) since the direction in which the user holds the housing is different from the operating direction of the operating cap.

SUMMARY OF THE INVENTION

The scope of the present invention is defined solely by the appended claims, and is not affected to any degree by the statements within this summary.

A first aspect of the present invention is a lancing device comprising:

a cover section, a part of which is provided with an opening;

a main body held on the cover section and configured to be movable in a predetermined direction from the opening relative to the cover section;

a lancing unit which is launched in the predetermined direction; and an operating section configured to launch the lancing unit when the operating section is pushed by applying a force in the predetermined direction, wherein the lancing unit is launched when the force is applied to the operating section in the predetermined direction with regulating a movement of the main body in the predetermined direction, and the main body moves, instead of pushing the operating section, by applying the force in the predetermined direction without regulating the movement of the main body in the predetermined direction.

A second aspect of the present invention is a lancing device comprising:

a main body comprising a housing, a biasing unit provided inside the housing and configured to launch a lancing unit in a predetermined direction, and a button for launching the lancing unit via the biasing unit when the button is pushed in the predetermined direction with a predetermined force; and a cover section to be held by a user when the user pushes the button, and which can hold the main body, with a force that is less than the predetermined force, so that at least part is covered by the housing, wherein the main body is movable in the predetermined direction relative to the cover section which holds the main body.

DETAILED DESCRIPTION OF THE PREFERRED EMBODIMENTS

Figure 1:
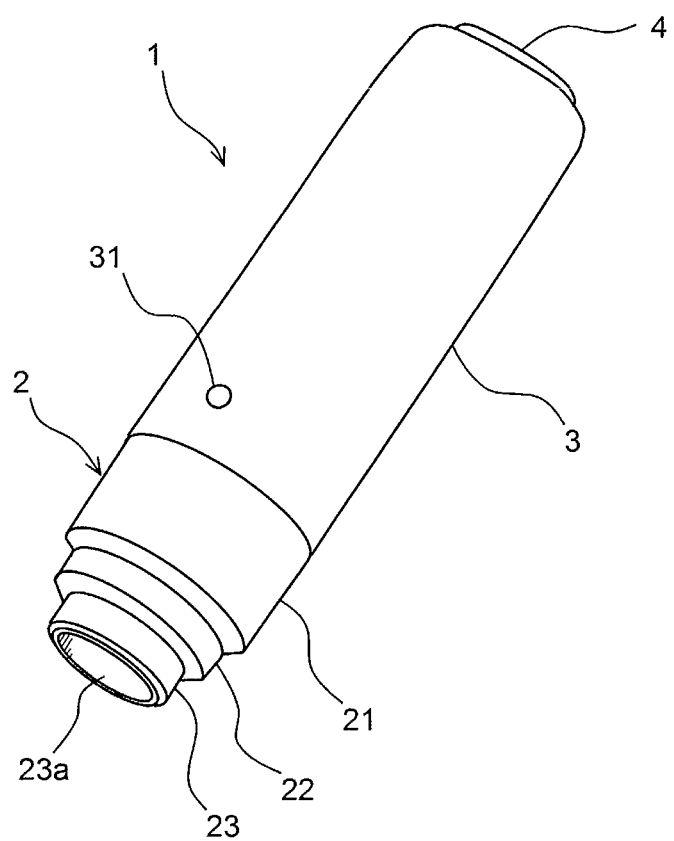
FIG. 1 is a perspective view of the external structure of a lancing device with the cover section closed.

The preferred embodiments of the present invention are described hereinafter with reference to the drawings.

The lancing device 1 of the present embodiment forms body fluid extraction holes (micropores) in the skin of a subject by installing a sterilized fine needle tip 6 so that the needles of the fine needle tip 6 abut the skin of the subject.

The body fluid (interstitial fluid) exuded from the micropores formed in the skin of the subject by the lancing device 1 and the fine needle tip 6 is collected in an extraction medium, the glucose concentration in the interstitial fluid is calculated by measuring the extraction medium by a glucose analyzer (not shown in the drawing) and estimating the AUC based on this calculated value so that a diabetic patient can, herself, monitor the estimated AUC to manage her condition.

Lancing Device Structure

Figure 2:
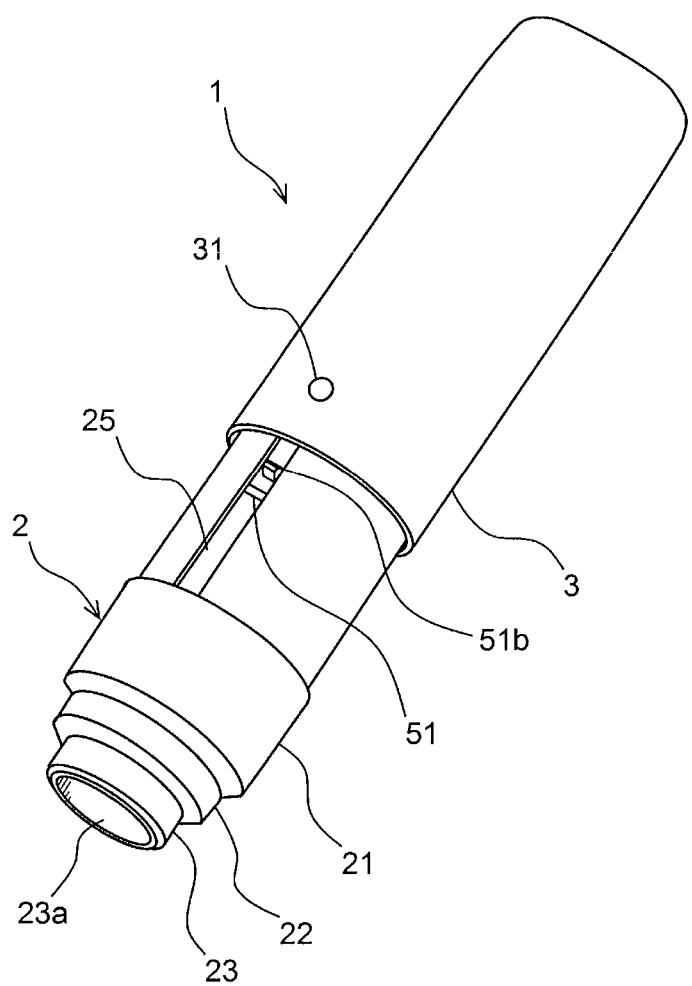
FIG. 2 is a perspective view of the external structure of a lancing device with the cover section opened.

The lancing device 1 forms a plurality of minute extraction pores through the stratum corneum of the epidermal layer of the skin but does not reach the vascular plexus in the dermis to extract interstitial fluid from the micropores. FIGS. 1 and 2 are perspective views showing the exterior structure of the lancing device of the present embodiment. The lancing device 1 is configured by a main body section 2 and a cover section 3 which covers the main body section 2, and is substantially cylindrical overall. The cover section 3 is capable of sliding in the longitudinal direction relative to the main body section 2. That is, the main body section 2 and the cover section 3 are relatively slidable in the longitudinal direction so that the main body section 2 can be pulled from the cover section 3 and the main body section 2 can be housed within the cover section 3. FIG. 1 shows the main body section 2 entirely housed within the cover section 3, whereas FIG. 2 shows the main body section 2 pulled from the cover section 3.

The main body section 2 has a cylindrical base 21. A cylindrical step portion 22 extends from the base 21 and has a diameter that is coaxial and slightly smaller than the diameter of the base 21, and a cylindrical ejecting portion 23 ultimately extends from the step portion 22 and has a diameter that is coaxial and slightly smaller than the diameter of the step portion 22. An ejection aperture 23a is provided in the ejecting portion 23, to allow the fine needle tip which forms micropores in the skin of the subject to be launched from the ejection aperture 23a.

A cylindrical inner housing portion 24, which has a diameter that is coaxial and smaller than the diameter of the base 21, extends from the base 21 from the side opposite the step portion 22. A mechanism for ejecting the fine needle tip is accommodated within the inner housing portion 24.

The cover section 3 is cylindrical with the same diameter as the base 21, and is mounted on the main body section 2 so as to cover the inner housing portion 24. The cover section 3 has an inner diameter that is slightly larger than the outer diameter of the inner housing portion 24, and is slidable in the longitudinal direction relative to the inner housing portion 24. In other words, the main body section 2 is slidable in the longitudinal direction relative to the cover section 3. When the inner housing portion 24 is entirely covered by the cover section 3 (the condition shown in FIG. 1 is hereinafter referred to as "closed condition"), the end of the cover section 3 abuts the base portion 21 (at this time, the position of the main body section 2 relative to the cover section 3 is hereinafter referred to as "first position"). A part of the inner housing portion 24 is exposed when the cover section 3 is moved relative to the main body section 2 in a direction that separates the base 21 and the cover section 3 from the closed condition. This condition (hereinafter referred to as "open condition") is shown in FIG. 2.

The cover section 3 is a part which the user holds when using the lancing device 1. The cover section 3 is cylindrical in shape as described above to be easy to hold by the user. The cover section 3 has an overall length of 100 mm and an external diameter of 30 mm so as to be easy to hold for the average adult. Note that the size and shape of the cover section 3 is not specifically limited to these dimensions, and preferably will be cylindrical with a length of 90 mm or more and less than 110 mm for ease of grasping in a hand of the user. When the cover section 3 is cylindrical, the major diameter is preferably 10 mm or more and less than 50 mm.

Figure 3:
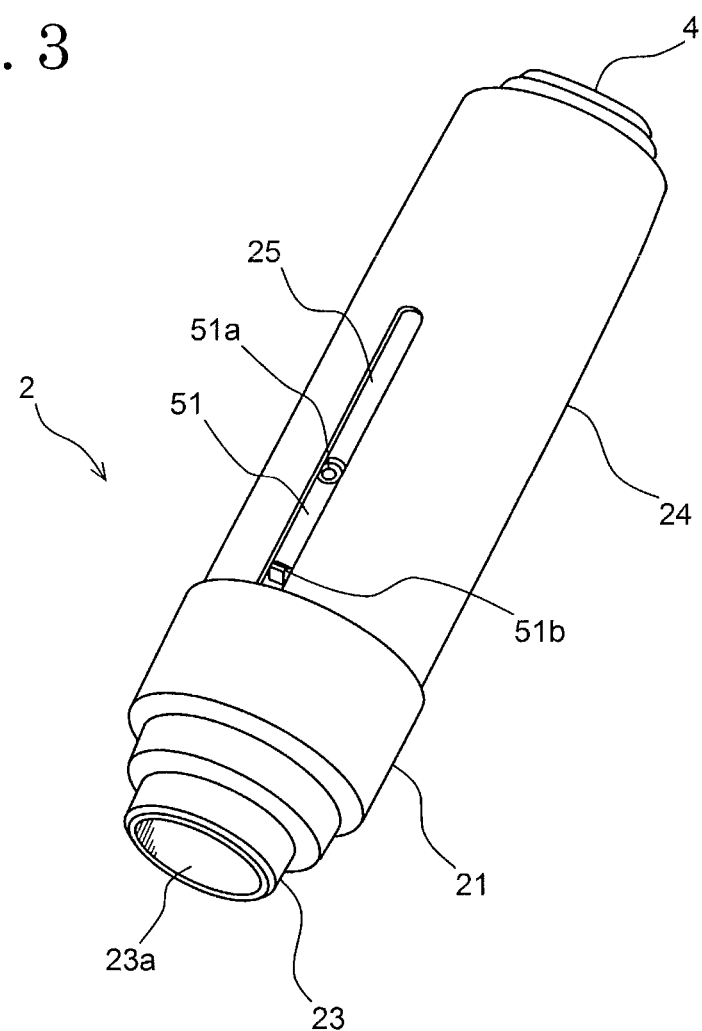
FIG. 3 is a perspective view of the external structure of the main body with the cover section removed.

FIG. 3 is a perspective view of the external structure of the main body section 2 with the cover section 3 removed. An operating section 4 is provided at the end of the main body section 2 on the opposite side from the ejecting portion 23. The operating section 4 may be, for example, a button. The main body section 2 is described below with the ejecting portion 23 side referred to as the downstream side and the operating section 4 side as the upstream side.

As shown in FIG. 3, the inner housing portion 24 is provided with a long slide hole in the longitudinal direction, that is, the vertical direction, of the inner housing portion 24. As shown in FIGS. 2 and 3, a pressing member 51 is provided within the inner housing portion 24. The pressing member 51 has a screw hole 51a, and a screw 31 for connecting the cover section 3 and the pressing member 51 is screwed into the screw hole 51a through a slide hole 25. The pressing member 51 is provided with a protrusion 51b which protrudes to the outside, and the protrusion 51b is inserted in the slide hole 25. That is, the screw 31 and the protrusion 51b are movable along the slide hole 25, thereby regulating the movement direction of the cover section 3 which is connected to the pressing member 51 in the vertical direction.

Figure 4:
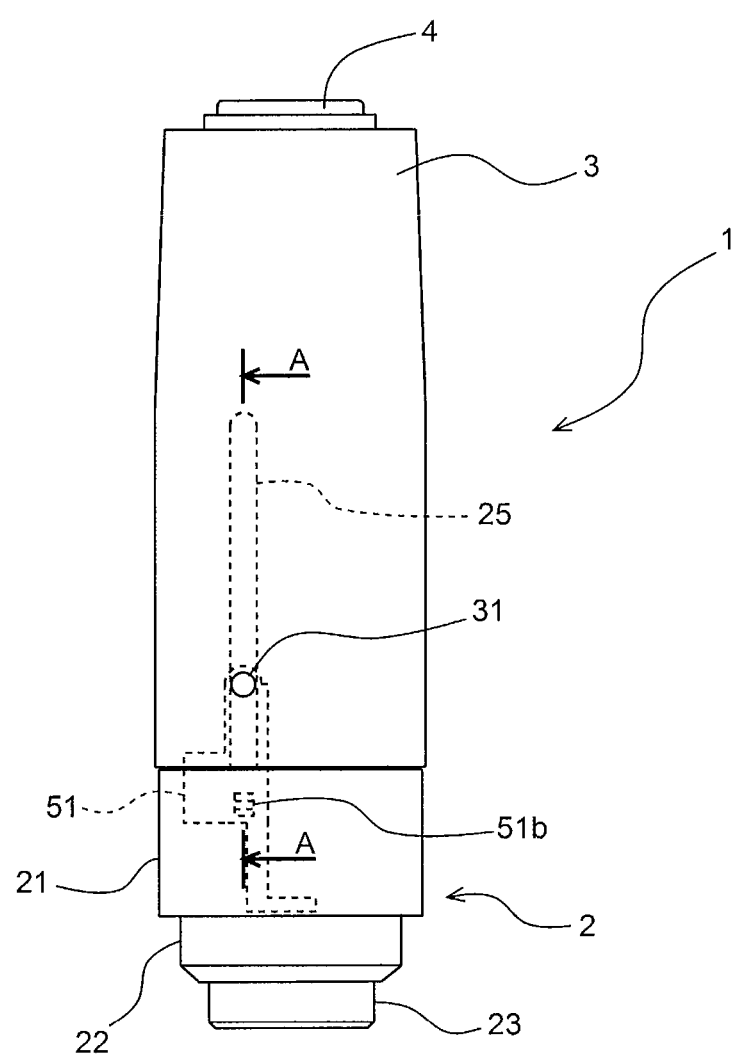
FIG. 4 is a frontal view showing the exterior of the lancing device in the closed condition.
Figure 5:
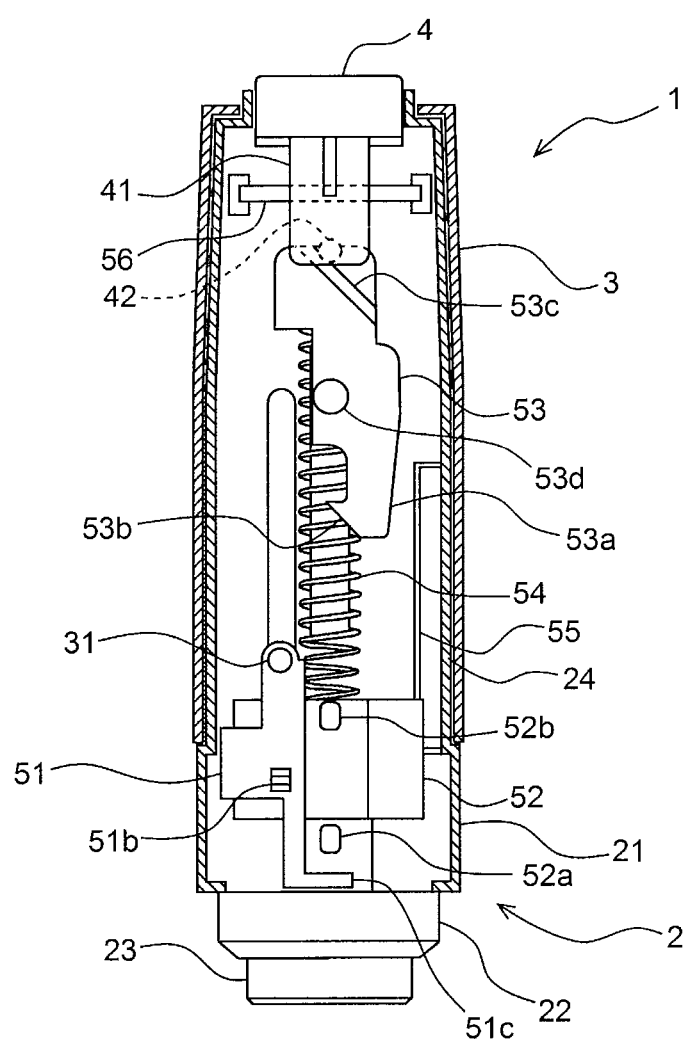
FIG. 5 is a front sectional view showing the interior of the lancing device in the closed condition.

FIG. 4 is a frontal view of the exterior of the lancing device in the closed condition, and FIG. 5 is a front sectional view showing the interior of the lancing device in the closed condition. The protrusion 51b is provided below the bottom end of the cover section 3. That is, the bottom end of the cover section 3 abuts the top end of the base 21 and the protrusion 51b intrudes to the inner side of the base 21 when the cover section 3 is in the closed condition.

The bottom end of the pressing member 51 is bent in an L-shape to form a contact portion 51c. A mounting member 52 for mounting the fine needle tip 6 is arranged inside the inner housing portion 24, and a compression spring 54 for exerting a force on the mounting member 52 is arranged above the mounting member 52.

The condition shown in FIG. 5 is a condition in which the compression spring 54 exerts a force on the mounting member 52 (referred to below as "de-energized condition"). That is, the position of the mounting member shown in FIG. 5 is the bottom limit position, and the length is the natural length such that a load is not exerted by the compression spring 54 when the mounting member 52 is at the bottom limit position.

The mounting member 52 has two protrusions 52a and 52b, as shown in FIG. 5. When the cover section 3 is lifted upward and the lancing device 1 transitions from the closed condition to the opened condition, the contact portion 51c of the pressing member 51 comes into contact with the protrusion 52a on the bottom side of the mounting member 52. The mounting member 52 is pressed by the pressing member 51 and moves upward when the cover section 3 is lifted. When the mounting member 52 moves upward, the compression spring 54 is compressed by the bottom end of the compression spring 54 being pressed upward by the mounting member 52. Thus, the compression spring 54 exerts a downward force on the mounting member 52.

Two opposed guide parts 55 are provided on the inner wall of the inner housing portion 24. FIG. 5 shows only one of the two guide parts 55. A gap extending in the vertical direction is formed between the two guide parts 55, and the mounting member 52 is arranged between the two guide parts 55. The movement direction of the mounting member 52 is regulated in the vertical direction by the gap between the two guide parts 55.

A locking member 53 is provided above the mounting member 52, as shown in FIG. 5. The locking member 53 is rotatable on an axis 53d which extends in the front-to-back direction. A hook 53a is provided on the locking member 53, and the locking member 53 exerts a force via a spring (not shown in the drawing) so that the hook 53a is positioned on the bottom side in the natural position.

Figure 6:
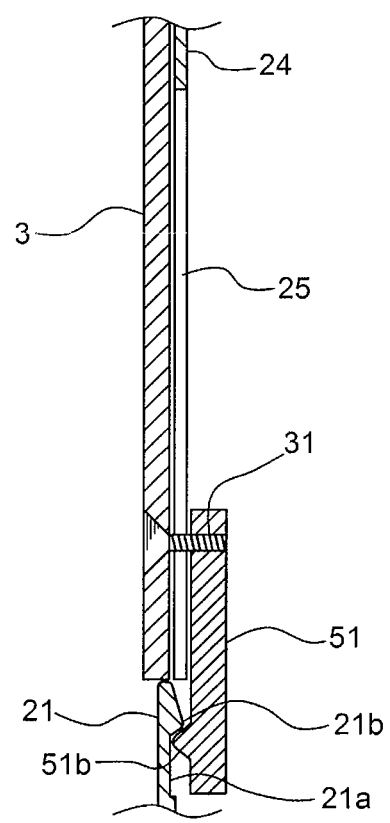
FIG. 6 is a side sectional view on the A-A line of FIG. 4.

FIG. 6 is a side sectional view on the A-A line of FIG. 4; when the lancing device 1 is in the closed condition, the bottom end of the cover section 3 and the top end of the base 21 are in contact or very near contact, as shown in FIG. 6. In this condition, the protrusion 51b of the pressing member 51 intrudes to the inner side of the base 21 as described above. A concavity 21a is formed on the inner side of the base 21, and the protrusion 51b engages the concavity 21a at this time. A convexity 21b is provided at the top side of the concavity 21a, such that the protrusion 51b must override the convexity 21b and move upward when the engagement is released from the condition of the protrusion 51b engages in the concavity 21a. That is, the protrusion 51b must override the convexity 21b for the lancing device 1 to transition from the closed condition to the opened condition. The force required to accomplish this override is 3 N in the present embodiment. Note that the force required to release the engagement of the main body section 2 and the cover section 3 of the lancing device 1 is not limited to 3 N, but preferably is 2 N or greater but less than 5 N.

Figure 7:
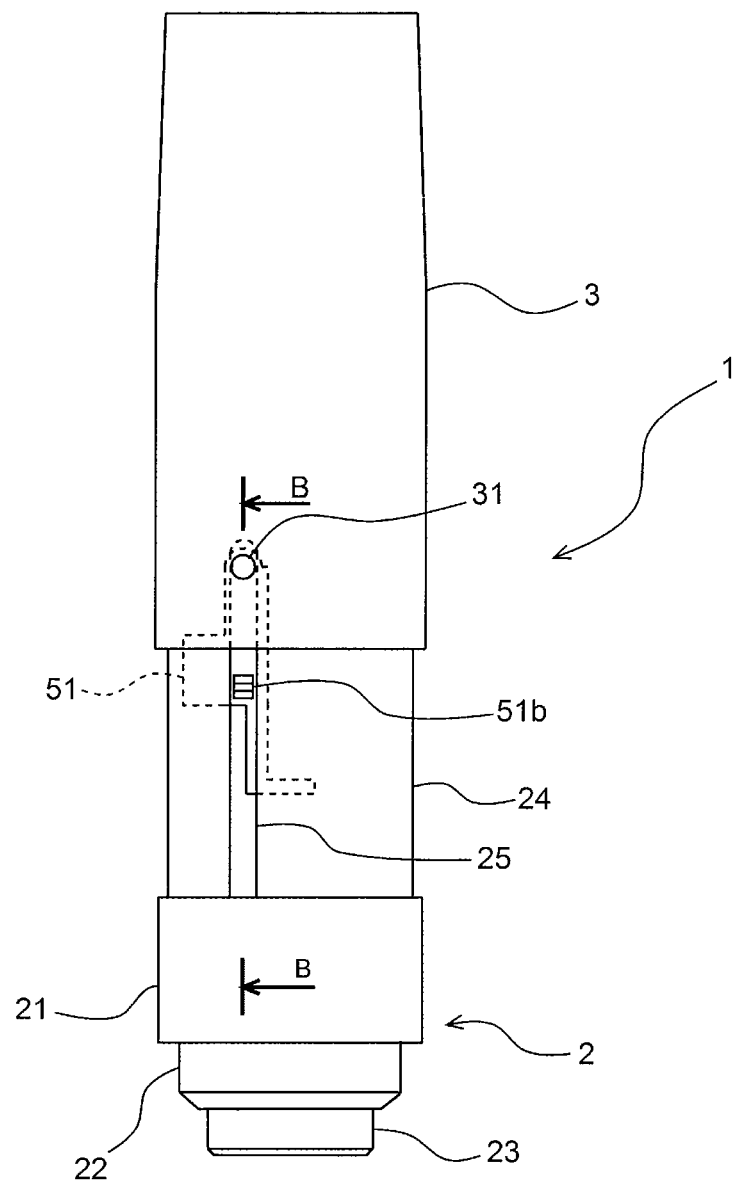
FIG. 7 is a frontal view showing the exterior of the lancing device in the open condition.
Figure 8:
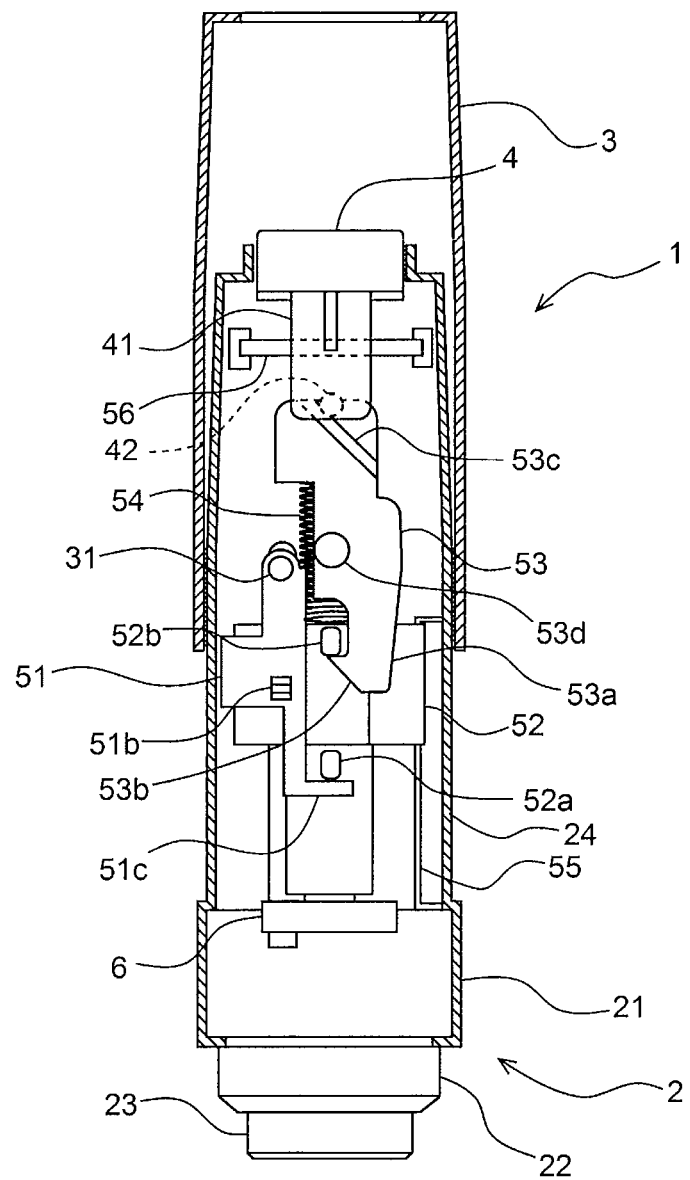
FIG. 8 is a front sectional view showing the interior of the lancing device in the open condition.
Figure 9:
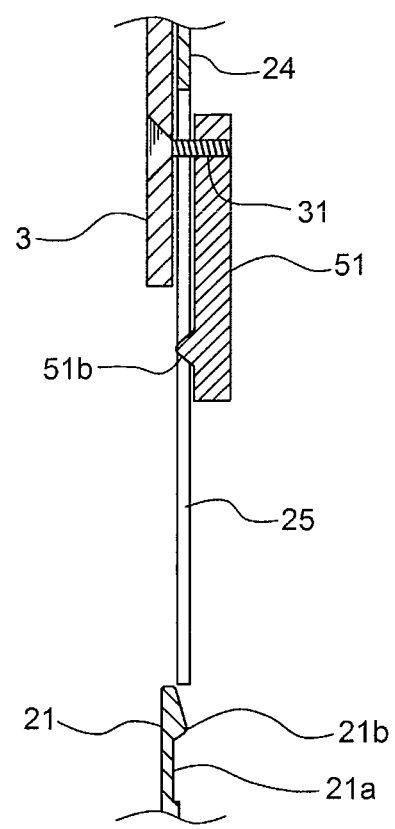
FIG. 9 is a side sectional view on the B-B line of FIG. 7.

FIG. 7 is a frontal view of the exterior of the lancing device in the opened condition, and FIG. 8 is a front sectional view showing the interior of the lancing device in the opened condition. FIG. 9 is a side sectional view on the B-B line of FIG. 7. When the cover section 3 is lifted upward relative to the main body section 2 with a force of 3 N or greater, the protrusion 51b which is engaged in the concavity 21a overrides the convexity 21b, and the engagement of the cover section 3 and the main body section 2 is released (refer to FIG. 9). When the cover section 3 is lifted upward, the bottom end of the cover section 3 separates from the top end of the base 21 and the inner housing section 24 is exposed (refer to FIG. 7). At this time, the pressing member 51 also moves upward together with the cover section 3 relative to the main body section 2, and the protrusion 51b is exposed from the slide hole 25 of the inner housing portion 24. The mounting member 52 is lifted upward when the cover section 3 is lifted upward while the contact portion 51c of the pressing member 51 contacts the protrusion 52a on the bottom side of the mounting member 52, as mentioned above.

An inclined portion 53b is provided on the bottom side of the hook 53a of the locking member 53. When the mounting member 52 moves upward within the inner housing portion 24, the mounting member 52 approaches the locking member 53 and the protrusion 52b on the top side of the mounting member 52 comes into contact with the inclined portion 53b of the locking member 53. Then, when the ascent of the mounting member 52 continues, the inclined portion 53b is pressed by the protrusion 52b and the locking member 53 is rotated on the pivot shaft 53d against the exerted force. Hence, when the protrusion 52b overrides the inclined surface 53b, the locking member 53 is rotated in the opposite direction by the exerted force and returned to the natural condition. The protrusion 52b therefore engages the hook 53a of the locking member 53 (refer to FIG. 8).

As shown in FIG. 7, when the cover section 3 is lifted upward relative to the main body section 2 until the screw 31 connecting the cover section 3 and the pressing member 51 is positioned near the top end of the slide hole 25 (at this time the position of the main body section 2 relative to the cover section 3 is referred to as "second position" below), the protrusion 52b of the mounting member 52 therefore engages the hook 53a of the locking member 53. At this time the mounting member 52 receives the force exerted by the compression spring 54 (referred to as "energized condition" below).

Figure 10:
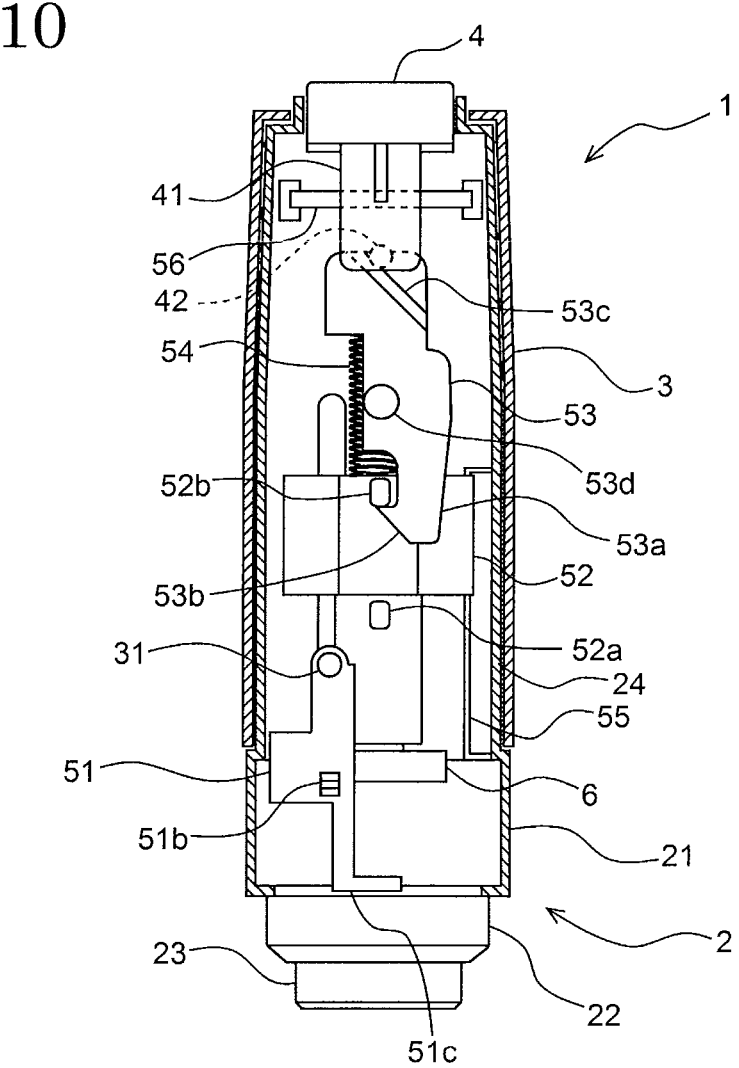
FIG. 10 is a front sectional view showing the interior of the lancing device with the cover section closed when the mounting member is in an energized state.

When the mounting member 52 is in the energized condition, the main body section 2 is movable between the first position and the second position. FIG. 10 is a front sectional view showing the interior of the lancing device 1 with the cover section 3 closed when the mounting member 52 is in the energized condition. When the main body section 2 is moved upward from the second position while the mounting member 52 is energized and the energized condition is locked by the locking member 53, the contact portion 51c of the pressing member 51 separates from the protrusion 52a of the mounting member 52 and moves downward relative to the protrusion 52a (the protrusion 52a moves upward relative to the contact portion 51c). That is, the cover section 3 is closed with the mounting member 52 in the energized condition.

The main body section 2 moves upward accurately relative to the cover section 3 because the pressing member 51 and the movement of the cover section 3 are regulated in the vertical direction by the slide hole 25 at this time. The upward movement of the main body section 2 causes the protrusion 51b of the pressing member 51 to override the convexity 21b provided on the inner side of the base 21, the protrusion 51b then engages the concavity 21a and the main body section 2 arrives at the first position. Hence, the condition shown in FIG. 8 transitions to the condition shown in FIG. 10.

Figure 11:
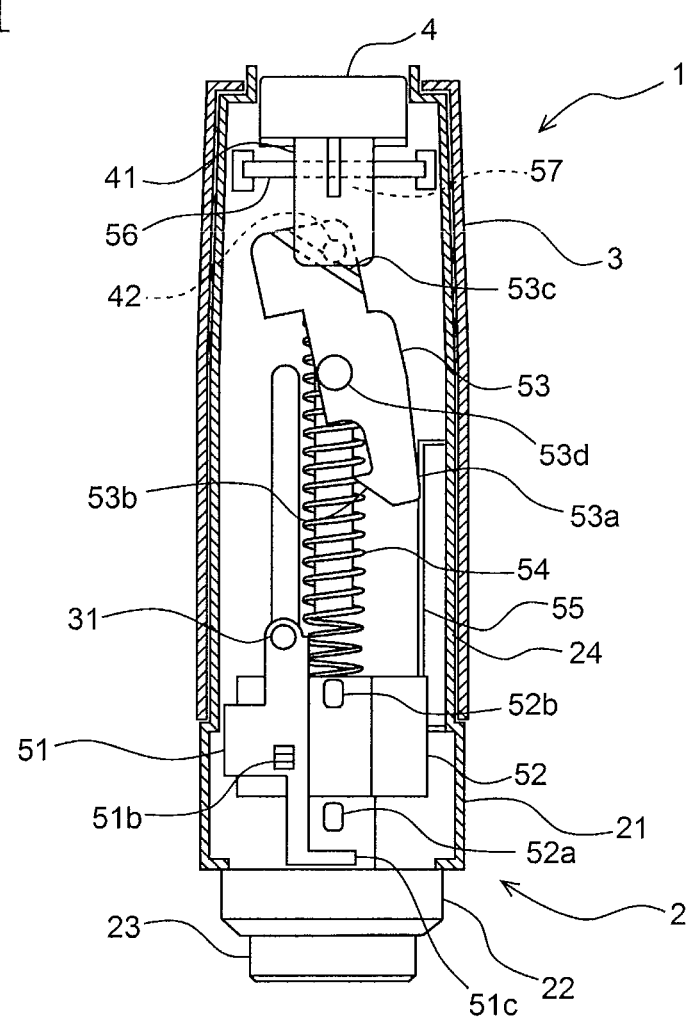
FIG. 11 is a front sectional view showing the interior of the lancing device in the operational condition.

When the mounting member 52 is in the energized condition and the main body section 2 is at the first position, the lancing device 1 enters the operational condition in which the device can be operated by the user. When the operating section 4 is operated downward while the lancing device 1 is in the operational condition (operating section 4 is pressed down), the lock held by the locking member 53 is released, the mounting member 52 is actuated by the force exerted by the compression spring 54, and the fine needle tip 6 is launched downward. FIG. 11 is a front sectional view showing the interior of the lancing device in the operational condition.

The operating section 4 is mounted on the inner housing portion 25 and moves in vertical directions. A support panel 56 which extends laterally is fixedly attached to the inner wall of the inner housing portion 25 at a position below the operating section 4. A vertical panel portion 41 is provided at the bottom of the operating section 4, and the panel portion 41 extends below the support panel 56.

A protrusion 42 is provided on the panel portion 41. An inclined portion 53c is provided on the surface of the locking member 53 which faces the panel portion 41. The inclined portion 53c of the locking member 53 comes into contact with the protrusion 42 of the panel portion 41. The operating section 4 is usually protrudes from the main body section 2 because the locking portion 53 receives an upward force via a spring through the protrusion 42 and the inclined portion 53c. When the operating section 4 is pressed downward, the panel portion 41 moves downward relative to the support panel 56, the inclined portion 53c is pressed down by the protrusion 42, and the locking member 53 is rotated on the pivot shaft 53d against the exerted force.

The force required to operate the operating section 4 in the downward direction, that is, the force necessary to press down the operating section 4 against the force exerted by the locking portion 53, is 6 N in the present embodiment. Note that the force required to press down the operating section 4 is not limited to 6 N, and such force is preferably 5 N or greater but less than 10 N inasmuch as the force necessary is at least greater than the force required to release the engagement between the main body section 2 and the cover section 3 of the lancing device 1 (a force of 3 N in the present embodiment).

When the operating section 4 is pressed down and the panel portion 41 moves downward, the panel portion 41 opposes the top part of the locking member 53. Then, when the descent of the operating section 4 continues, the inclined portion 53c is pressed by the protrusion 42 and the locking member 53 is rotated on the pivot shaft 53d against the exerted force. Hence, the engagement is released between the protrusion 52b of the mounting member 52 and the hook 53a of the locking member 53, the mounting member 52 with the fine needle top 6 mounted thereon is forced downward by the compression spring 54, and the fine needle tip 6 is launched.

Lancing Device Operation

The operation of the lancing device 1 is described below. The subject first mounts the fine needle tip 6 on the mounting member 52 from the ejection aperture 23a.

The subject then shifts the lancing device 1 from the de-energized condition to the energized condition. That is, the subject holds the cover section 4 of the lancing device 1 in the hand (for example, the right hand) and grasps the base 21 of the main body section 2 with the other hand (for example, the left hand), then moves the cover section 3 relative to the base 21 so as to pull the closed cover section 3 from the base 21. The main body section 2 is thus moved from the first position to the second position.

While the main body section 2 moves from the first position to the second position, the pressing member 51 moves upward inside the inner housing portion 24, the contact portion 51c comes into contact with the protrusion 52a of the mounting member 52, and the mounting member 52 is pressed upward by the pressing member 51. The compression spring 54 is therefore compressed, and the mounting member 52 is ultimately pulled up against the force exerted by the compression spring 54. The protrusion 52b on the top side of the mounting member 52 comes into contact with the inclined portion 53b of the locking member 53, the inclined portion 53b is pressed by the protrusion 52b, and the locking member 53 is rotated on the pivot shaft 53d. When the protrusion 52b overrides the inclined portion 53b, the locking member 53 returns to the natural condition and the protrusion 52b engages the hook 53a of the locking member 53. Hence, the mounting member 52 becomes energized.

The subject then moves the main body section 2 from the second position to the first position relative to the cover section 3 so as to close the cover section 3 of the energized lancing device 1. That is, the subject moves the cover section 3 with one hand to bring it near the base 21 which is held in the other hand so that there is contact or near contact between the bottom end of the cover section 3 and the top end of the base 21. Hence, the lancing device 1 becomes operational.

When the lancing device 1 becomes operational, the subject holds the cover section 3 in one hand (for example, the right hand), and presses the bottom end of the lancing device 1, that is, the end provided with the ejection aperture 23a of the ejecting portion 23, against the body (for example, the left arm) of the subject. Thus, the main body 2 of the lancing device 1 is pressed upward, that is, the mounting member 52 (fine needle tip 6) is pressed in the opposite direction to the direction in which the force is exerted by the compression spring 54, and the downward movement of the main body section 2 is regulated.

As described above, the operating section 4 is operated by the thumb of the hand in which the subject holds the cover section 3 when the main body section 2 is pushed upward. When a downward force is applied to the operating section 4, this force is transmitted to the main body section 2 through the support panel 56. That is, the downward force on the main body section 2 functions as a force in the direction of separation from the cover section 3. However, since the main body section 2 is pressed against the body of the subject at this time, a reaction force to the downward force is generated, and the main body section 2 does not move relative to the cover section 3 so as to remain stationary at the first position.

As described above, a force of 6 N is required to operate the operating section 4. Therefore, when a downward force of 6 N or greater is applied to the operating section 4, the locking member 53 rotates on the pivot shaft 53d. This action releases the lock of the locking member 53, the mounting member 52 is actuated by the force exerted by the compression spring 54, and the fine needle tip 6 is launched downward. A plurality of fine needles protrude from the bottom surface (the surface facing the skin, referred to as "micropore forming surface" below) of the fine needle tip 6. The fine needles of the fine needle tip 6 have a length (for example 0.3 mm) sufficient to pass through the stratum corneum of the epidermal skin but not reach the vascular plexus in the dermis. The micropore forming surface of the fine needle tip 6 abuts (impacts) the skin of the subject and forms a plurality of micropores in the skin of the subject.

The operation of the lancing device 1 is described below when a force is applied downward on the operating section 4 while the bottom end of the operational lancing device 1 is not pressed against the body of the subject, that is, the downward movement of the main body section 2 is not regulated. When a downward force is applied to the operating section 4 due to the subject trying to operate the operating section 4 or inadvertently touching the operating section 4 when the main body section 2 of the lancing device 1 is not being pressed upward, this force is transmitted to the main body section 2 through the support panel 56. That is, the downward force on the main body section 2 functions as a force in the direction of separation from the cover section 3.

At this time a force of 3 N is required to release the engagement between the base 21 and the protrusion 51b of the pressing member 51; since a force of 6 N is required to operate the operating section 4, the operating section 4 does not operate when a downward force of 3 N or greater is applied to the operating section 4, and the engagement between the base 21 and the protrusion 51b is not released. Therefore, the main body section 2 moves from the first position to the second position relative to the cover section 3, and the lancing device 1 is opened. At this time the fine needle tip 6 is not launched because the operating section 4 does not operate. That is, according to the lancing device 1 of the present embodiment, when the bottom end of the lancing device 1 is not pressed against the body of the subject, the mechanism which launches fine needle tip 6 of the lancing device 1 will not operate even when a downward force is applied to the operating section 4 due to misuse or the like, and the main body section 2 and the cover section 3 are pulled apart. The user inadvertently launching the fine needle tip 6 is therefore prevented.

Other Embodiments

Note that although the embodiment described above is configured with the operating section 4 provided at the end on the opposite side from the ejection aperture 23*a* of the lancing device 1, the present invention is not limited to this configuration. The position of the operating section is discretionary insofar as it is operational in the same direction as the direction of separation of the main body section 2 from the cover section 3. For example, the operating section may be provided on a side surface of the cover section 3.

Although the drive source of the mounting member 52 and the fine needle tip 6 mounted thereon is a compression spring 54 in the above embodiment, the present invention is not limited to this configuration. An elastic body other than a compression spring, such as rubber, tension spring, air spring or the like also may be used as the drive source of the mounting member 52 and the fine needle tip 6. Furthermore, a power generator such as a pneumatic cylinder or more may be used, rather than an elastic body, as the drive source of the mounting member 52 and the fine needle tip 6, wherein the power generator generates a drive force in response to the operation of the operating section 4 to drive the mounting member 52 and the fine needle tip 6.

Although a force of 3 N is required to release the engagement between the cover section 3 and the main body section 2, and a force of 6 N is required to operate the operating section 4 in the embodiment described above, the present invention is not limited to this configuration. However, it is preferable that the difference between the force required to operate the operating section 4 and the force required to release the engagement between the cover section 3 and the main body section 2 is 1 N or greater but less than 6 N. When a downward force is applied to the operating section 4 while the main body section 2 of the operational lancing device 1 is not being pressed upward, the mechanism which launches the fine needle tip 6 of the lancing device 1 is reliably prevented from operating and the main body section 2 and the cover section 3 can be pulled apart by because the difference between the force required to operate the operating section 4 and the force required to release the engagement between the cover section 3 and the main body section 2 is 1 N or greater. Furthermore, handling complexity is caused by an extreme difference between the force required to operate the operating section 4 and the force required to release the engagement between the cover section 3 and the main body section 2 can be avoided because difference between the force required to operate the operating section 4 and the force required to release the engagement between the cover section 3 and the main body section 2 is less than 6 N.

Although the above embodiment has been described in terms of piercing the skin of a subject by a fine needle tip 6, the present invention is not limited to this configuration. A configuration which lances by mounting a lancing unit with a conventional needle may also be applied.

Although the above embodiment is described in terms of operation by the subject herself, the present invention is not limited to this configuration. The lancing device also may be operated by a person other than the subject.

What is claimed is:

1. A lancing device for puncturing a skin of a subject, comprising:
   a tubular cover section having a first opening at one end and a second opening at the other end;
   a tubular main body having one end and the other end opposite to the one end and arranged to directly slide into and out of the first opening of the cover section, such that the one end of the main body is arranged inside of the cover section, the other end of the main body is arranged outside of the cover section, and the main body is configured to be movable in a predetermined direction relative to the cover section;
   a lancing unit housed in the main body and launched in the predetermined direction from the other end of the main body;
   an operating section installed to the one end of the main body and configured to be pushed by applying a force in the predetermined direction through the second opening of the cover section;
   a biasing unit installed in the main body and configured to bias the lancing unit in the predetermined direction; and
   a locking unit installed in the main body and configured to lock a bias of the biasing unit and to release a lock of the biasing unit;
   wherein the locking unit releases the lock, the biasing unit biases the lancing unit, the lancing unit is launched and the main body remains at a first position relative to the cover section when the subject presses the other end of the tubular main body against the skin of the subject and applies a force to the operating section in the predetermined direction through the second opening, and
   wherein when the other end of the tubular main body is not pressed against of the skin of the subject, the main body is configured to move from the first position to a second position relative to the cover section without releasing the lock of the locking unit and the lancing unit is not launched in response to the force is applied to the operating section in the predetermined direction through the second opening.

2. The lancing device of claim 1, wherein the biasing unit is an elastic body.

3. The lancing device of claim 1, wherein the main body is configured to return the first position relative to the cover section after the main body has moved from the first position to the second position relative to the cover section to cause the biasing unit to transition from a non-energized state to an energized state and cause the locking unit to lock the biasing unit and maintain the lock.

4. The lancing device of claim 1, wherein the main body comprises a guide part for guiding the movement in the predetermined direction relative to the cover section between the first position and the second position.

5. The lancing device of claim 1, wherein
   the cover section is configured to be held by a subject; and
   the operating section is configured to be operated by a hand of the subject which holds the cover section.

6. The lancing device of claim 1, wherein the lancing unit is a fine needle tip having a plurality of needles.

7. The lancing device of claim 1, wherein the second opening is smaller than the first opening, and the tubular main body is not able to be inserted into the cover section through the second opening.

8. A lancing device for puncturing a body of a subject, comprising:
- a tubular cover section having a first opening at one end and a second opening at the other end; and
- a tubular main body having one end and the other end opposite to the one end and comprising a tubular housing arranged to directly slide into and out of the first opening of the cover section, such that the one end of the main body is arranged inside of the cover section and the other end of the main body is arranged outside of the first opening of the cover section, a biasing unit provided inside the housing to launch a lancing unit from the other end of the main body in a predetermined direction, and a button for launching the lancing unit via the biasing unit, wherein
- the main body comprises a guide part configured to guide a movement of the one end the main body relative to the cover section in the predetermined direction between a first position in the cover section and a second position closer to the first opening of the cover section than the first position,
- the lancing unit is launched from the other end of the main body and the one end of the main body remains at the first position when the subject presses the other end of the tubular main body against the body of the subject and pushes the button in the predetermined direction through the second opening, and
- the lancing unit is not launched from the other end of the main body and the one end of the main body moves from the first position to the second position when the subject pushes the button in the predetermined direction through the second opening without pushing the main body against the body of the subject.

9. The lancing device of claim 8, configured so that the biasing unit launches the lancing unit in the predetermined direction when the button is pushed in the predetermined direction while the main body is pressed in the opposite direction to the predetermined direction when the subject presses the other end of the tubular main body against the body of the subject.

10. The lancing device of claim 8 further comprising a locking unit for locking a bias of the biasing unit, and unlocking the lock in response to pushing the button, wherein
- the locking unit unlocks the bias and the lancing unit is launched to the predetermined direction when the button is pushed in the predetermined direction with the subject pushing the main body against the body of the subject in the opposite direction to the predetermined direction,
- and without pushing the main body against the body of the subject the main body moves relative to the cover section from the first position to the second position without releasing the lock of the locking unit when the button is pushed in the predetermined direction.

11. The lancing device of claim 10, wherein the main body is configured return to the first position relative to the cover section after the main body has moved from the first position to the second position relative to the cover section to cause the biasing unit to transition from a non-exerting state to an energized state, and cause the locking unit to lock the biasing unit and maintain the lock.

12. The lancing device of claim 8, wherein the biasing unit is an elastic body.

13. The lancing device of claim 8, wherein the lancing unit is a fine needle tip having a plurality of needles.

14. A lancing device for puncturing a skin of a subject, comprising:
- a cover section having a tubular shape, a first opening at one end and a second opening at the other end;
- a tubular main body having one end and the other end opposite to the one end and comprising a tubular housing arranged to directly slide into and out of the first opening of the cover section, such that the one end of the main body is arranged inside of the cover section and the other end of the main body is arranged outside of the first opening of the cover section, a biasing unit provided inside the housing and configured to launch a lancing unit from the other end of the main body in a predetermined direction, and a button for launching the lancing unit via the biasing unit wherein
- the main body comprises a guide part configured to guide a movement of the one end the main body relative to the cover section in the predetermined direction between a first position in the cover section and a second position closer to the first opening of the cover section than the first position,
- the lancing unit is launched from the other end of the main body and the one end of the main body remains at the first position when an user pushes the button in the predetermined direction through the second opening with pushing the main body in an opposite direction to the predetermined direction, and
- the lancing unit is not launched from the other end of the main body and the one end of the main body moves from the first position to the second position when the user pushes the button in the predetermined direction through the second opening without pushing the main body in the opposite direction to the predetermined direction;
- a biasing unit installed in the tubular inner housing and configured to bias the lancing unit in the predetermined direction; and
- a locking unit installed in tubular inner housing and configured to lock a bias of the biasing unit and to release a lock of the biasing unit in response to an operation of the operating section;
- wherein the locking unit releases the lock, the biasing unit biases the lancing unit, the lancing unit is launched and main body remains stationary at the first position relative to the cover section when the force is applied to the operating section in the predetermined direction through the second opening and the subject presses the other end of the main body against the skin of the subject, and
- the main body moves from the first position to a second position relative to the cover section without releasing the lock of the locking unit, and the lancing unit is not launched when the subject presses the other end of the main body against the skin of the subject and the force is applied to the operating section in the predetermined direction through the second opening.

15. The lancing device of claim 14, wherein the tubular main body further comprises a tubular base, and wherein the first and second opening of the cover section are smaller than the tubular base.

16. The lancing device of claim 15, wherein the tubular base is not inserted into the cover section when the tubular inner housing is inserted into the cover section through the first opening.

17. The lancing device of claim 14, wherein the main body comprises a guide part for guiding the movement in the predetermined direction relative to the cover section.

* * * * *